United States Patent [19]

Kudo et al.

[11] 3,966,821

[45] June 29, 1976

[54] PROCESS FOR PREPARING 1-TETRAHYDRONAPHTHALONE

[75] Inventors: Ken-Ichi Kudo, Niihama; Tadayuki Ohmae, Kobe; Yoshiki Toyoshima; Sumio Hara, both of Niihama, all of Japan

[73] Assignee: Sumitomo Chemical Company, Limited, Osaka, Japan

[22] Filed: Feb. 26, 1975

[21] Appl. No.: 553,200

[30] Foreign Application Priority Data
Feb. 26, 1974 Japan.............................. 49-23150

[52] U.S. Cl.............................. 260/590 R; 252/467
[51] Int. Cl.$^2$.......................................... C07C 49/76
[58] Field of Search........................ 260/590, 590 R

[56] References Cited
UNITED STATES PATENTS
3,404,185  10/1968  Thomas et al...................... 260/590

OTHER PUBLICATIONS

Kirk–Other, Encyclopedia of Chemical Technology, 2nd edition, vol. 5, pp. 495–496.

*Primary Examiner*—James O. Thomas, Jr.
*Assistant Examiner*—James H. Reamer
*Attorney, Agent, or Firm*—Sughrue, Rothwell, Mion, Zinn & Macpeak

[57] ABSTRACT

A process for preparing 1-tetrahydronaphthalone which comprises oxidizing tetrahydronaphthalene by a liquid phase oxidation with molecular oxygen or a molecular oxygen-containing gas in the presence of a catalyst system comprising a chromium salt of naphthenic acid and an alkyl-substituted pyridine compound.

2 Claims, No Drawings

PROCESS FOR PREPARING 1-TETRAHYDRONAPHTHALONE

BACKGROUND OF THE INVENTION

1. Field of the Invention

This invention relates to a process for preparing 1-tetrahydronaphthalone which comprises oxidizing tetrahydronaphthalene by a liquid phase oxidation with molecular oxygen or a molecular oxygen-containing gas. More particularly, this invention relates to an improved process for preparing 1-tetrahydronaphthalone in a high selectivity from tetrahydronaphthalene which comprises oxidizing tetrahydronaphthalene by a liquid phase oxidation with molecular oxygen or a molecular oxygen-contianing gas in the presence of a catalyst system comprising a chromium salt of naphthenic acid and an alkyl-substituted pyridine compound having the formula

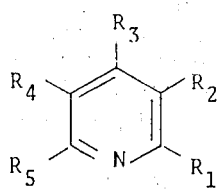

wherein $R_1$, $R_2$, $R_3$, $R_4$ and $R_5$, which can be the same or different, each represents a hydrogen atom or an alkyl group having 1 to 5 carbon atoms and at least one of $R_1$, $R_2$, $R_3$, $R_4$ and $R_5$ is an alkyl group, thereby minimizing the formation of 1-tetrahydronaphthol as a by-product.

2. Description of the Prior Art

It is well known that 1-tetrahydronaphthalone can be converted by dehydrogenation into α-naphthol which is an industrially important raw material having a wide variety of utilities, e.g., as an intermediate of dyes, a raw material of agricultural agents, etc.

Hitherto, various processes for producing 1-tetrahydronaphthalone from tetrahydronaphthalene have been studied and known to the art, for example, (1) a process comprising air-oxidation of tetrahydronaphthalene in the presence of a cobalt salt or an iron salt, (2) a process comprising air-oxidation of tetrahydronaphthalene using a catalyst system of a chromium acetate-2-methyl-5-ethylpyridine complex as disclosed in U.S. Pat. No. 3,404,185, and (3) a process comprising oxidation of tetrahydronaphthalene in the presence of a catalyst system comprising a cobalt naphthenate having incorporated therein an amine, a pyridine compound and the like.

In the prior art process (1) above, the selectivity to 1-tetrahydronaphthalone is low thereby producing 1-tetrahydronaphthaol as a by-product in a large proportion. The resulting 1-tetrahydronaphthol has little utility in industry and, in addition, causes various undesirable problems, for example, clogging of reactors and conduits in a purification step of the resulting product such as distillation since 1-tetrahydronaphthol tends to be converted further into secondary by-products through dehydration, dimerization or the like.

Accordingly, the formation of a large amount of 1-tetrahydronaphthol in the production of 1-tetrahydronaphthalone is one of the serious problems. Thus, it is very important in the liquid phase oxidation of tetrahydronaphthalene to minimize as low as possible the formation of 1-tetrahydronaphthol as a by-product and to produce 1-tetrahydronaphthalone in high selectivity, i.e., to increase a molar ratio of 1-tetrahydronaphthalone/1-tetrahydronaphthol in the reaction mixture obtained by the liquid phase oxidation of tetrahydronaphthalene.

In the trial of the prior art process (2) above by the present inventors, this process revealed a 1-tetrahydronaphthalone/1-tetrahydronaphthol molar ratio of 19.4 under conditions which would provide the optimum result in a batch process, as shown hereinafter in greater detail in Comparative Examples, but the process revealed a markedly low molar ratio of 1-tetrahydronaphthalone/1-tetrahydronaphthol, i.e., 3,9, in a continuous process which is considered to be a practically important process in the production of 1-tetrahydronaphthalone on an industrial scale. Further, this prior art process was found to have a serious disadvantage as an industrial process in that, since chromium acetate used in this process does not dissolve in tetrahydronaphthalene, a solid precipitate is formed during the oxidation reaction and deposited in the reactor and the conduits thereby making it difficult to operate the process for a long period of time.

SUMMARY OF THE INVENTION

As a result of various investigations for eliminating the disadvantages associated by the prior art processes, it was found that the yield of 1-tetrahydronaphthalone produced by the liquid phase oxidation of tetrahydronaphthalene can markedly be increased when the oxidation is carried out in the presence of a catalyst system comprising a chromium salt of naphthenic acid and an alkyl-substituted pyridine compound having the formula described above.

That is, the present invention provides a process for preparing 1-tetrahydronaphthalone in high selectivity with a high molar ratio of 1-tetrahydronaphthalone/1-tetrahydronaphthol and with a minimum precipitation formation of undesirable insoluble solids, which comprises oxidizing tetrahydronaphthalene in a liquid phase with molecular oxygen or a molecular oxygen-containing gas in the presence of a catalyst system comprising a chromium salt of naphthenic acid and an alkyl-substituted pyridine compound as defined herein.

DETAILED DESCRIPTION OF THE INVENTION

In the present invention, a chromium salt used as one component of the catalyst system is chromous naphthenate, chromic naphthenate or a mixture thereof, preferably chromic naphthenate because of its stability.

The pyridine compound used in the present invention as another component of the catalyst system is at least one compound represented by the following formula

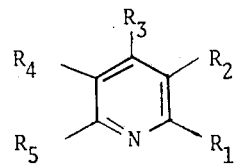

wherein $R_1$, $R_2$, $R_3$, $R_4$ and $R_5$, which can be the same or different, each represents a hydrogen atom or an alkyl group having 1 to 5 carbon atoms and at least one of $R_1$, $R_2$, $R_3$, $R_4$ and $R_5$ is an alkyl group. Representative pyridine compounds which can be used in the present invention are methylpyridine ($\alpha$-, $\beta$-, or $\gamma$-picoline), dimethylpyridine (2,3-, 2,4-, 2,5-, 2,6-, or 3,4-lutidine), trimethylpyridine (2,3,4-, 2,3,5-, 2,3,6-, 2,4,5- or 2,4,6-collidine), 2,3,4,5-tetramethylpyridine, ethylpyridines, diethylpyridines, butylpyridines, 2-methyl-5-ethylpyridine and the like. In the process of this invention, the molar ratio of 1-tetrahydronaphthalone/1-tetrahydronaphthol tends to increase as the number of alkyl substituents on the pyridine nucleus increases and, therefore, dimethylpyridines and trimethylpyridines are preferably used in practising the process of this invention.

In carrying out the process of this invention, tetrahydronaphthalene is oxidized by introducing molecular oxygen or a molecular oxygen-containing gas into a solution of a chromium salt of naphthenic acid and an alkyl-substituted pyridine compound in tetrahydronaphthalene, either in a batch manner or a continuous manner.

Additionally, the chromium salt used in the present invention is highly soluble in the starting tetrahydronaphthalene. Therefore, the process is homogeneous and the reaction type is preferably continuous.

The manner of addition of the catalyst system is not critical, and the catalyst system can be incorporated into the oxidation system in a manner conventionally used in general liquid phase air-oxidations. For example, the chromium naphthenate and the pyridine compound can be added to tetrahydronaphthalene separately or as a mixture thereof.

The chromium naphthenate can be used in a concentration of about 0.1 to 500 ppm, preferably 0.5 to 250 ppm, in tetrahydronaphthalene calculated as chromium ion.

The amount of the pyridine compound is not critical, but the compound is generally used at a concentration of about 0.1 to about 10 mol%, preferably 0.5 to 5 mol%, in tetrahydronaphthalene. However, it is to be noted that the amount of the pyridine compound is not limited to the above range and can be varied optionally with other parameters of the oxidation reaction.

Molecular oxygen or the molecular oxygen-containing gas can be preferably used in a proportion of about 0.01 to about 10 based on a molecular oxygen/tetrahydronaphthalene molar ratio.

The liquid phase oxidation of the present invention can be carried out at a temperature of about room temperature (about 20° – 30°C) to about 250°C, preferably 50° to 100°C, under atmospheric pressure or pressurized conditions, advantageously under a pressure of from atmospheric pressure to about 20 kg/cm$^2$ for a period of about 0.2 to about 10 hours, preferably 0.5 to 5 hours.

According to the process of this invention, the selectivity to 1-tetrahydronaphthalone, i.e., the conversion of tetrahydronaphthalene into desired 1-tetrahydronaphthalone, is markedly improved and yet an amount of 1-tetrahydronaphthol formed as a by-product is markedly minimized as compared with the conventional tetrahydronaphthalene oxidation process. Thus, the process of this invention provides an oxidation product having a significantly increased molar ratio of 1-tetrahydronaphthalone/1-tetrahydronaphthol thereby eliminating the disadvantages of the conventional process and, therefore, is extremely advantageous as a process for producing 1-tetrahydronaphthalone from tetrahydronaphthalene on an industrial scale.

The present invention is further illustrated by the following Examples, but these Examples are given for illustrative purposes only and are not to be construed as limiting the scope of this invention. Unless otherwise indicated, all parts, percents, ratios and the like are by weight.

EXAMPLE 1

A glass cylindrical reactor having a diameter of 40 mm and a length of 600 mm was charged with 430 g of tetrahydronaphthalene 4.3 g of 2,4-lutidine (1.2 mol%) and chromium(III) naphthenate (5ppm calculated as Cr ion), the reaction mixture was a homogeneously transparent solution and then air was introduced from the bottom of the reactor at a rate of 10 Nl/hr. at a temperature of 80°C under atmospheric pressure. After allowing the mixture to react for 3 hours, the reaction mixture was analyzed by gas chromatography, and the gas chromatographed sample was further subjected to IR and NMR spectral analyses (hereinafter the same). The results obtained are shown in Table I below.

EXAMPLES 2 TO 5 AND COMPARATIVE EXAMPLES 1-3

The procedure described in Example 1 was repeated but using a catalyst shown in Table 1 below in place of 2,4-lutidine and chromium(III) naphthenate and using a reaction temperature of 60°C in Example 2 and a reaction temperature of 125°C in Comparative Example 3.

The results obtained are also shown in Table 1.

Table 1

| Example No. | Catalyst | Conversion of Tetrahydronaphthalene (%) | Selectivity to 1-Tetrahydronaphthalone (%) | Selectivity to 1-Tetrahydronaphthol (%) | Molar Ratio of 1-Tetrahydronaphthalone/1-Tetrahydronaphthol |
|---|---|---|---|---|---|
| 1 | Chromium (III) Naphthenate (5 ppm as Cr ion) 2,4-Lutidine (1.2 mol%) | 6.1 | 95.9 | 3.2 | 30.0 |
| 2 | Chromium (III) Naphthenate (50 ppm as Cr ion) 2,4-Lutidine (1.2 mol%) | 5.7 | 96.5 | 3.0 | 32.2 |
| 3 | Chromium (III) Naphthenate (5 ppm as Cr ion) $\alpha$-Picoline (2.4 mol%) | 6.7 | 94.4 | 4.7 | 20.1 |
| 4 | Chromium (III) Naphthenate (5 ppm as Cr ion) | 6.7 | 96.3 | 2.9 | 33.2 |

Table 1-continued

| | | | | | |
|---|---|---|---|---|---|
| | 2,6-Lutidine (1.2 mol%) | | | | |
| 5 | Chromium (III) Naphthenate (50 ppm as Cr ion) 2,4,6-Collidine (1.2 mol%) | 6.8 | 97.0 | 2.2 | 44.1 |

| Comparative Example No. | Catalyst | Conversion of Tetrahydronaphthalene | Selectivity to 1-Tetrahydronaphthalone | Selectivity to 1-Tetrahydronaphthol | Molar Ratio of 1-Tetrahydronaphthalone/1-Tetrahydronaphthol |
|---|---|---|---|---|---|
| | | (%) | (%) | (%) | |
| 1 | None | 1.3 | 2.4 | 1.9 | 1.3 |
| 2 | Chromium (III) Naphthenate (5 ppm as Cr ion) | 5.5 | (Product predominantly comprises tetralin peroxide) 62.6 | 36.9 | 1.7 |
| 3 | 13% Aqueous Solution of Chromic Acetate (100 ppm as Cr ion) 2-Methyl-5-ethylpyridine (1.2 mol%) | 6.1 | 93.0 | 6.2 | 15.0 |

EXAMPLE 6

The same reactor as used in Example 1 was charged with 233 g of tetrahydronaphthalene, 4.7 g (2.4 mol%) of 2,4-lutidine and chromium(III) naphthenate (100 ppm calculated as Cr ion) which was completely dissolved in tetrahydronaphthalene, and oxygen was introduced from the bottom of the reactor at a rate of 30 Nℓ/hr. at a temperature of 80°C under atmospheric pressure. After allowing the mixture to react for 0.5 hours, the reaction mixture was analyzed in the same manner as described in Example 1. The results obtained are shown in Table 2 below.

COMPARATIVE EXAMPLE 4

The procedure described in Example 6 was repeated but using a catalyst which had previously been prepared by mixing 4.7 g (2.4 mol%) of 2-methyl-5-ethylpyridine and a 13% aqueous solution of chromic acetate (100 ppm calculated as Cr ion) in place of 2,4-lutidine and chromium(III) naphthenate. The results obtained are shown in Table 2 below.

A large part of chromic acetate was deposited on the bottom and the wall of the reactor.

Table 2

| Example or Comparative Example No. | Conversion of Tetrahydronaphthalene | Selectivity to 1-Tetrahydronaphthalone | Selectivity to 1-Tetrahydronaphthol | Molar Ratio of 1-Tetrahydronaphthalone/1-Tetrahydronaphthol |
|---|---|---|---|---|
| | (%) | (%) | (%) | (%) |
| Example 6 | 14.3 | 95.0 | 3.1 | 30.6 |
| Comparative Example 4 | 19.2 | 93.1 | 4.8 | 19.4 |

EXAMPLE 7

A stainless steel cylindrical reactor having a diameter of 50 mm and a length of 800 mm was charged continuously with 430 g/hr. of tetrahydronaphthalene, 4.3 g (1.2 mol%)/hr. of 2,4-lutidine and chromium(III) naphthenate (50 ppm calculated as Cr ion) while introducing air at a rate of 70 Nℓ/hr. at a temperature of 80°C and the reaction mixture was drawn from the top of the reactor. The results obtained on analyses of the resulting reaction mixture are shown in Table 3 below.

EXAMPLE 8

A vertical type stainless steel cylindrical reactor having a diameter of 350 mm and a length of 2600 mm was charged continuously with 39 kg/hr. of tetrahydronaphthalene, 0.39 kg/hr. (1.2 mol%) of 2,4-lutidine and chromium(III) naphthenate (50 ppm calculated as Cr ion) while introducing air at a rate of 8 Nm³/hr. at a temperature of 80°C, and the reaction mixture was drawn from the outlet at a distance of 1740 mm from the bottom of the reactor. The results obtained on analyses of the resulting reaction mixture are shown in Table 3 below.

COMPARATIVE EXAMPLE 5

The procedure described in Example 7 was repeated but using 8.0 g/hr. (2.0 mol%) of 2-methyl-5-ethylpyridine and a 5.2% aqueous solution of chromic acetate (100 ppm calculated as Cr ion) in place of 2,4-lutidine and chromium(III) naphthenate and using a reaction temperature of 140°C. The results obtained are shown in Table 3 below.

Table 3

| Example or Comparative Example No. | Conversion of Tetrahydronaphthalene | Selectivity to 1-Tetrahydronaphthalone | Selectivity to 1-Tetrahydronaphthol | Molar Ratio of 1-Tetrahydronaphthalone/1-Tetrahydronaphthol |
|---|---|---|---|---|
| | (%) | (%) | (%) | |

Table 3-continued

| Example or Comparative Example No. | Conversion of Tetrahydronaphthalene | Selectivity to 1-Tetrahydronaphthalone | Selectivity to 1-Tetrahydronaphthol | Molar Ratio of 1-Tetrahydronaphthalone/1-Tetrahydronaphthol |
| --- | --- | --- | --- | --- |
| Example 7 | 12.1 | 93.7 | 4.1 | 22.8 |
| Example 8 | 11.0 | 93.8 | 3.8 | 24.7 |
| Comparative Example 5 | 12.8 | 74.3 | 18.9 | 3.9 |

While the invention has been described in detail and with reference to specific embodiments thereof, it will be apparent to one skilled in the art that various changes and modifications can be made therein without departing from the spirit and scope thereof.

What is claimed is:

1. In a process for preparing 1-tetrahydronaphthalone by a liquid phase oxidation of tetrahydronaphthalene with molecular oxygen or a molecular oxygen containing gas in the presence of a catalyst, wherein
   a. said molecular oxygen or said molecular oxygen containing gas is used in a proportion of about 0.01 to about 10 based on a molecular oxygen/tetrahydronaphthalene molar ratio;
   b. said oxidation is conducted at a temperature of about room temperature to about 250°C under a pressure between atmospheric and about 20 kg/cm² for a period of about 0.2 to about 10 hours; and
   c. said oxidation is conducted by introducing said molecular oxygen or said molecular oxygen containing gas into a solution of said catalyst in tetrahydronaphthalene in a batch manner or a continuous manner;
   the improvement comprising conducting said liquid phase oxidation in the presence of a catalyst system consisting essentially of
   a. chromic naphthenate, chromous naphthenate or a mixture thereof in a concentration of about 0.1 to about 500 ppm in the tetrahydronaphthalene calculated as chromium ion, together with
   b. an alkyl-substituted pyridine compound represented by the formula,

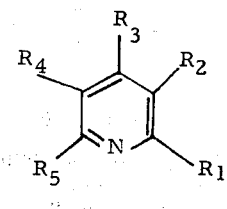

wherein $R_1$, $R_2$, $R_3$, $R_4$ and $R_5$, which can be the same or different, each represents a hydrogen atom or an alkyl group having 1 to 5 carbon atoms and at least one of $R_1$, $R_2$, $R_3$, $R_4$ and $R_5$ is an alkyl group, said pyridine compound being present in a concentration of about 0.1 to about 10 mol % in tetrahydronaphthalene.

2. The process according to claim 1, wherein said pyridine compound is α-picoline, β-picoline, γ-picoline, 2,3-lutidine, 2,4-lutidine, 2,5-lutidine, 2,6-lutidine, 3,4-lutidine, 2,3,4-collidine, 2,3,5-collidine, 2,3,6-collidine, 2,4,6-collidine, 2,4,5-collidine, 2,3,4,5-tetramethylpyridine, an ethylpyrdine, a diethylpyridine, a butylpyridine, 2-methyl-5-ethylpyridine or a mixture thereof.

* * * * *